United States Patent [19]

Jarsch et al.

[11] Patent Number: 5,308,770
[45] Date of Patent: May 3, 1994

[54] CLONING AND OVEREXPRESSION OF GLUCOSE-6-PHOSPHATE DEHYDROGENASE FROM *LEUCONOSTOC DEXTRANICUS*

[75] Inventors: Michael Jarsch, Bad Heilbrunn; Gunter Lang, Tutzing, both of Fed. Rep. of Germany

[73] Assignee: Boehringer Mannheim GmbH, Mannheim-Waldhof, Fed. Rep. of Germany

[21] Appl. No.: 22,096

[22] Filed: Feb. 25, 1993

Related U.S. Application Data

[62] Division of Ser. No. 739,071, Jul. 30, 1991, Pat. No. 5,229,286.

[30] Foreign Application Priority Data

Jul. 30, 1990 [DE] Fed. Rep. of Germany ....... 4024158

[51] Int. Cl.$^5$ ..................... C12P 21/06; C12N 15/00
[52] U.S. Cl. .................................. 435/190; 536/23.2; 435/302.1; 435/252.3; 435/252.33; 435/65.1
[58] Field of Search ..................... 536/23.2; 435/69.1, 435/252.3, 252.33, 320.1

[56] References Cited

FOREIGN PATENT DOCUMENTS 2641285 7/1990 France .

OTHER PUBLICATIONS

Federation of European Biochemical Societies, vol., 211, No. 2, Jan. 1987, pp. 243–246, "Sequence identity between a lysince-containing peptide from Leuconostoc mesenteroides glucose—6—phosphate dehydrogenase and an dehydrogenase", Bhadbhade, M. M. et al.
Journal of Bacteriology, vol. 169, No. 1, Jan. 1987, American Society for Microbiology, pp. 334–339, "Expression of the gene for NAD-dependent glucose—6—phosphate dehydrogenase from Leuconostoc mesenteroides cloned in *Escherichia coil* K-12", Murphy, N. B. et al.
Biochemical Society Transactions, vol. 17, No. 2, Apr. 1989, The Biochemical Society, London, GB, pp. 313–315, "Glucose—6—phosphate dehydrogenase from Leuconostoc mesenteroides", Levy, R. H.
Journal of Biological Chemistry, vol. 266, No. 20, 15, Jul. 1991, Baltimore, US, pp. 13028–13034, "Cloning of the gene and amino acid sequence for glucose—6—phosphate dehydrogenase from Leuconostoc mesenteroides", Lee, T. W. et al.

*Primary Examiner*—Robert A. Wax
*Assistant Examiner*—David B. Schmickel
*Attorney, Agent, or Firm*—Nikaido, Marmelstein, Murray & Oram

[57] ABSTRACT

The invention concerns a glucose-6-phosphate dehydrogenase which contains the amino acid sequence shown in SEQ ID NO:1 as well as a DNA coding for it and a process for the isolation of an enzyme according to the present invention.

17 Claims, 1 Drawing Sheet

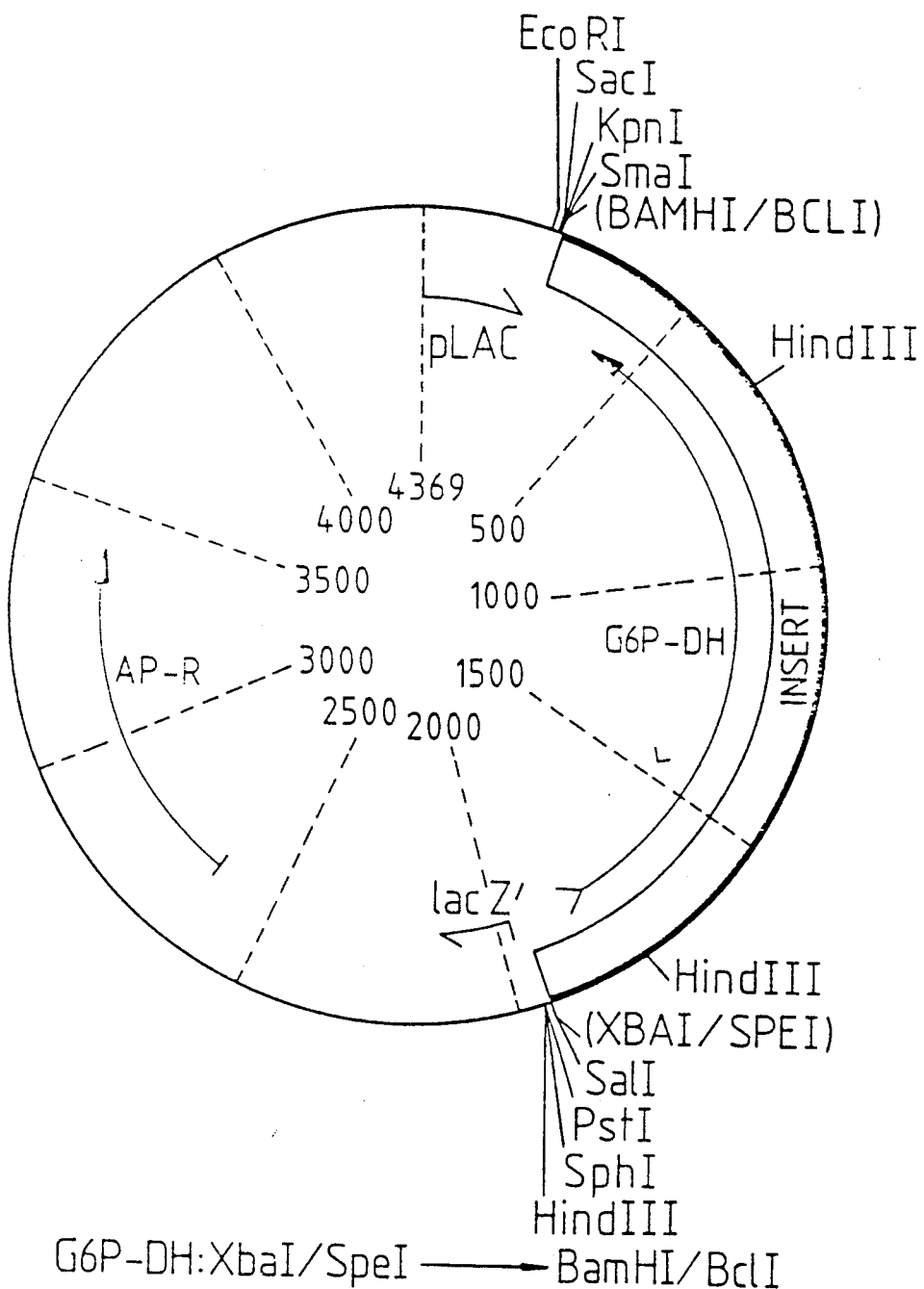

CLONING AND OVEREXPRESSION OF GLUCOSE-6-PHOSPHATE DEHYDROGENASE FROM *LEUCONOSTOC DEXTRANICUS*

This is a division of application Ser. No. 07/737,071 filed Jul. 30, 1991, now U.S. Pat. No. 5,229,286, issued Jul. 20, 1993.

Glucose-6-phosphate dehydrogenase (G6P-DH) catalyzes the first step in the oxidative metabolism of glucose. In this process glucose-6-phosphate is oxidized to gluconic acid-6-phosphate while $NAD^+$ or/and $NADP^+$ is reduced as the cosubstrate. The oxidation of glucose ultimately results in the production of pentose sugars for the nucleic acid metabolism.

Glucose-6-phosphate dehydrogenase can for example be isolated from *Leuconostoc mesenteroides*. This enzyme can use $NAD^+$ as well as $NADP^+$ as cofactor, in contrast to the enzyme from yeast which is specific for $NADP^+$. The enzyme is present as a dimer consisting of two identical monomeric subunits with a molecular weight of 55000 D. Its specific activity at 25° C. is 550 U/mg.

Disadvantages of the process for isolating G6P-DH from bacteria of the genus Leuconostoc are inter alia that the lactic acid bacteria have complex nutrient requirements and therefore grow only slowly in those nutrient media used on a large technical scale and only reach a low cell density. In addition the content of G6P-DH in the biomass is only very low when using Leuconostoc (about 1% of the total cell protein). Thus, large fermentation dimensions are necessary in order to provide adequate amounts of G6P-DH. Moreover, it is only possible to obtain an enzyme preparation with a low specific activity because of the large amounts of foreign protein.

The most important disadvantage of the known G6P-DH from Leuconostoc bacteria is, however, their low temperature stability.

The object of the present invention was therefore to provide a glucose-6-phosphate dehydrogenase which no longer has the disadvantages of the state of the art.

The object according to the present invention is achieved by the provision of a glucose 6-phosphate dehydrogenase which contains the amino acid sequence shown in SEQ ID NO:1 and is obtainable from Leuconostoc mesenteroides, subspecies dextranicus (DSM 20187) which is denoted *Leuconostoc dextranicus* in the following.

In addition the present invention also provides a DNA which contains a sequence encoding the enzyme according to the present invention shown in SEQ ID NO:1 or a corresponding sequence within the scope of the degeneracy of the genetic code.

The recombinant DNA according to the present invention was isolated by screening a *L. dextranicus* (DSM 20187) gene bank with a suitable oligonucleotrde probe which is described below in more detail.

When the recombinant DNA according to the present invention is expressed in *E. coli* cells it surprisingly turned out that even small fermentation volumes are sufficient to provide the desired amount of enzyme. Compared to the isolation of G6P-DH from Leuconostoc, a reduction in the fermentation volume by a factor 1:500 to 1:1000 is achieved. Moreover, G6P-DH preparations are obtained in high purity, i.e. with a specific activity of ca. 900 U/mg, with a less extensive purification procedure. However, a surprisingly special characteristic of the recombinant enzyme according to the present invention is a substantially improved temperature stability compared to the known enzyme when isolated from *E. coli*. An additional advantage of the recombinant enzyme in contrast to the known enzyme from Leuconostoc is that it does not react with glucose. This well-known unspecific reaction of the Leuconostoc enzyme with glucose (Olive and Levy, Biochemistry 6 (1967), 730) has previously been a major drawback in carrying out enzyme tests since this could lead to false results in determinations because of the presence of glucose in blood, serum or plasma. Finally the recombinant enzyme also differs from the known G6P-DH in that the $K_m$ value for $NADP^+$ is different and the effect of activators and inhibitors (e.g. phosphate, glycerol, magnesium ions, hydrogen carbonate) is different.

The present invention also provides a recombinant vector which contains one or several copies of the recombinant DNA according to the present invention. Such a vector is intended to enable the expression of the recombinant DNA according to the present invention in foreign host organisms. The vector according to the present invention can be a vector which integrates into the chromosomal DNA of the host cell (e.g. bacteriophage lambda), it can, however, also be present extrachromosomally in the host cell (plasmid). The vector according to the present invention is preferably a plasmid.

The vector according to the present invention can be a eukaryotic as well as a prokaryotic vector, it is, however, preferably a prokaryotic vector, i.e. it is suitable for multiplication in prokaryotic host organisms. The recombinant vector has particularly preferably an origin of replication which is active in *E. coli* i.e. it can be multiplied in *E. coli*.

In a particularly preferred embodiment the recombinant vector according to the present invention contains the nucleic acid sequence coding for the glucose-6-phosphate dehydrogenase which is under the control of a promoter sequence from *Leuconostoc dextranicus* which functions in *E. coli* and which is included in the first 122 nucleotides (upstream of the G6P-DH gene) of the nucleic acid sequence shown in SEQ ID NO:1.

In order to exhibit promoter properties it is not necessary that the DNA region has exactly this sequence of 122 nucleotides. Derived sequences or fragments of this sequence which have promoter properties are also suitable. Under a derived biologically active sequence in the sense of the invention it is therefore understood that individual nucleotides or short nucleotide sequences from the promoter sequence can be deleted, substituted or inserted and namely in such a way that the promoter activity of the sequence is preserved. A person skilled in the art does indeed know that for a promoter it is not necessary to conserve the whole sequence but rather only particular partial regions. In prokaryotic promoter sequences these are in particular the regions at $-35$ and at $-10$ with respect to the transcription start.

Thus the invention also includes a recombinant DNA which has the first 122 nucleotides of the nucleic acid sequence shown in SEQ ID NO:1 or a sequence derived therefrom with promoter properties. Surprisingly this Leuconostoc promoter also results in a good protein expression in *E. coli*. Thus, this promoter can also be used for the expression of heterologous genes, i.e. genes which are different from the G6P-DH gene, in gram-negative bacteria, preferably *E. coli* bacteria.

The present invention in addition provides a microorganism which is transformed with a recombinant vector according to the present invention. In this connection it is preferably a gram-negative bacterium, particularly preferably an *E. coli* bacterium.

The recombinant DNA according to the present invention can be obtained by (1) isolating chromosomal *Leuconostoc dextranicus* DNA and cleaving it with a suitable restriction enzyme, (2) incorporating the cleaved *L. dextranicus* DNA into a vector, transforming a suitable organism with the vector and producing a gene bank in this way, (3) screening the gene bank from step (2) with a nucleic acid probe which has a sequence which is specific for the glucose-6-phosphate dehydrogenase gene whereby these probes are constructed in lactic acid bacteria with respect to the codon usage and (4) analyzing the clones of the gene bank which react positively with the probe from step (3).

The chromosomal *L. dextranicus* (DSM 20187) DNA can be isolated by combined polyethylene glycol/lysozyme treatment and subsequent incubation with proteinase K.

The cleavage of the isolated *L. dextranicus* DNA with a suitable restriction enzyme, the ligation of the cleaved DNA into a suitable cloning vector and the transformation of a suitable organism with the recombinant cloning vector for the production of a gene bank can be carried out in a manner familiar to one skilled in the area of molecular biology. The next step is the examination of the gene bank produced in this way with a nucleic acid probe which has a sequence specific for the glucose-6-phosphate dehydrogenase gene.

A peptide sequence of G6-PDH from L. mesenteroides with a lysine residue (*) which can be pyridoxylated is knotn from Haghighi et al., Biochemistry 21 (1982), 6415-6420. This sequence is as follows (SEQ. ID NO:9 and SEQ. ID NO:5): Phe-Leu-Lys*-Ser-Pro-Ser-Tyr-(Asp/Val)-Lys. However, it was not possible to derive an oligonucleotide probe from this sequence which can be used to find a hybridization signal in the *L. dextranicus* gene bank.

Bhadbhade et al., FEBS Letters 211 (1987), 243-246 discloses a peptide sequence from the active centre of the G6P-DH from *L. mesenteroides* with a high homology to human G6P-DH. The oligonucleotide probe mentioned in Example 2 with a length of 72 bases (SEQ ID NO:2) was produced from the multitude of oligonucleotide probes which can be constructed from this peptide sequence.

Screening the *L. dextranicus* DNA gene bank with this oligonucleotide in a 5' end-labelled form finally produced a positive clone which allowed the determination of the sequence of the *L. dextranicus* G6P-DH gene.

The DNA sequence of the G6P-DH gene from *L. dextranicus* was determined according to the method of Sanger. It is shown in SEQ ID NO:1.

SEQ ID NO:1 also shows the amino acid sequence of the G6P-DH from *L. dextranicus* which was determined from it. From this it can be seen that the amino acid sequence of the enzyme according to the present invention does not correspond to the sequence of the *L. mesenteroides* enzyme described in FEBS Letters 211 (1987), 243-246 in 6 out of 42 positions.

In addition the invention includes a process for the production of a G6P-DH with the amino acid sequence shown in SEQ ID NO:1 in which (1) a suitable host organism is transformed with a DNA or a vector according to the present invention which contains one or several copies of this DNA, (2) the transformed host organism is cultured in a suitable medium and (3) the protein is isolated from the medium or the cells.

The expression of the recombinant protein according to the present invention in a transformed host organism, preferably in a prokaryotic host organism, particularly preferably in an *E. coli* cell, is in principle possible under the control of any suitable promoter. Thus, in *E. coli* an expression of the G6P-DH is e.g. possible under the control of heterologous promoters such as e.g. the tac promoter, mgl promoter or pfl promoter. However, the expression is preferably carried out constitutively under the control of a Leuconostoc promoter, particularly preferably under the control of the promoter sequence shown in SEQ ID NO:1 or of a promoter sequence derived therefrom (corresponding to the first 122 nucleotides of SEQ ID NO:1). The plasmid pUC G6P-DH 1.8 which is shown in FIG. 1 is most preferred.

The commercially available *E. coli* strain HB 101 was chosen as a suitable *E. coli* host strain. When transforming *E. coli* HB 101 with pUC G6P-DH 1.8 it was found that the plasmid has a high stability in the cell and the expression of the G6P-DH can be carried out over several passages even without selection pressure.

It is intended to elucidate the present invention by the following examples in conjunction with SEQ ID NO:1 and 3 as well as FIG. 1.

SEQ ID NO:1 shows the nucleotide sequence of the Leuconostoc DNA insertion in pUC G6P-DH 1.8 in which the first 122 bases upstream of the coding region for the *L. dextranicus* G6P-DH promoter and the bases 123-1580 represent the nucleotide sequence of the *L. dextranicus* G6P-DH gene which codes for a protein with the amino acid sequence which is also shown, SEQ ID NO:3 shows the oligonucleotide probe for the part of the G6P-DH gene from Leuconostoc mesenteroides which codes for a region of the active centre of the G6P-DH of *L. mesenteroides* which has a high homology to human G6P-DH.

FIG. 1 shows the plasmid pUC-G6P-DH 1.8.

EXAMPLE 1

Isolation of Chromosomal DNA from *Leuconostoc dextranicus*

Genomic DNA is isolated from *Leuconostoc dextranicus* according to the following method:

*Leuconostoc dextranicus* (DSM 20187) is cultured at 30° C. in APT medium (Merck No. 10454). The cells from 100 ml culture broth are centrifuged down, washed in 10 ml 20 mmol/l Tris/HCl pH 8.0 and finally resuspended in 15 ml of this buffer solution. After addition of 5 ml 24 % (w/v) polyethylene glycol 6000 and 20 mg lysozyme it is incubated for 16 h at 4° C. The cell lysis is carried out by addition of 1 ml 20 % (w/v) SDS. 2 mg protease K are added and incubated for 60 min at 37° C. The further purification of the DNA is carried out by sequential phenol and chloroform extraction, treatment with RNAse A (0.5 mg/60 min at 37° C.), renewed phenol and chloroform extraction and a final ethanol precipitation.

We claim:

1. Isolated DNA, comprising the region of the nucleic acid sequence shown in SEQ ID NO:1 coding for a glucose-6-phosphate dehydrogenase enzyme or another nucleic acid sequence encoding the same enzyme.

2. Recombinant vector which contains one or several copies of a DNA as claimed in claim 1.

3. Recombinant vector as claimed in claim 2, which is a prokaryotic vector.

4. Recombinant vector as claimed in claim 3, which contains an origin of replication which is active in *Escherichia coli*.

5. Recombinant vector as claimed in claim 2, wherein the nucleic acid sequence coding for the glucose-6-phosphate dehydrogenase is under the control of a Leuconostoc promoter.

6. Recombinant vector as claimed in claim 5, wherein the promoter is the native promoter of the glucose-6-phosphate dehydrogenase gene and comprises the first 122 bases of the nucleic acid sequence shown in SEQ ID NO:1 or comprises a sequence derived therefrom with native glucose-6-phosphate dehydrogenase gene promoter properties.

7. Plasmid pUC-B6P-DH 1.8.

8. Isolated DNA, that comprises a native promoter of the glucose-6-phosphate dehydrogenase gene and the first 122 bases of the nucleic acid sequence shown in SEQ ID NO:1 or comprises a sequence derived therefrom with native glucose-6-phosphate dehydrogenase gene promoter properties.

9. Microorganism, wherein it is transformed with a DNA as claimed in claim 1 or with a recombined vector as claimed in claim 2.

10. Microorganism as claimed in claim 9, which is a gram-negative bacterium.

11. Microorganism as claimed in claim 10, which is an *Escherichia coli*.

12. Process for the isolation of a DNA as claimed in claim 1, wherein
   (1) *Leuconostoc dextranicus* (DSM 20187) DNA is isolated and cleaved with a suitable restriction enzyme,
   (2) the cleaved *L. dextranicus* DNA is incorporated into a vector, a suitable host organism is transformed with the vector and a gene bank is produced in this way,
   (3) the gene bank from (2) is screened with a nucleic acid probe which has a sequence specific for the glucose-6-phosphate dehydrogenase gene and
   (4) the clones of the gene bank which react positively with the probe (3) are selected.

13. Process as claimed in claim 12, wherein a probe is used which is 50 to 80 nucleotides long.

14. Process as claimed in claim 12 or 13, wherein *Escherichia coli* is used as the host organism.

15. Process for the isolation of glucose-6-phosphate dehydrogenase, wherein
   (1) a suitable host organism is transformed with a DNA as claimed in claim 1 or with a vector as claimed in claim 2,
   (2) the transformed host organism is cultured in a suitable medium and
   (3) the glucose-6-phosphate dehydrogenase is concentrated from the medium or the cells.

16. Process as claimed in claim 15, wherein a prokaryotic host organism is used.

17. Process as claimed in claim 16, wherein *Escherichia coli* is used as the host organism.

* * * * *

UNITED STATES PATENT AND TRADEMARK OFFICE
CERTIFICATE OF CORRECTION

PATENT NO. : 5,308,770
DATED : May 3, 1994
INVENTOR(S) : Michael JARSCH et al

It is certified that error appears in the above-identified patent and that said Letters Patent is hereby corrected as shown below:

On the title page, Item [62], change " 739,071 " to -- 73<u>7</u>,071 --.

Signed and Sealed this

Fifteenth Day of November, 1994

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1696 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 123..1580

( x i ) SEQUENCE DESCRIPTION: SEQ ID NO:1:

```
TCTAGTCATT TAATCAATTT TTGACTTGTT CAACGCTTAA TATGTTTGTG AATCCCGTAC        60

TTTTCCAGAC CTTTTTGCGT TATAATGGAG AGTGAATTTA ATTATAATAT AAGGGGAACA       120

TC ATG GTT TCA GAA ATC AAA ACG TTG GTA ACT TTC TTT GGC GGA ACT          167
   Met Val Ser Glu Ile Lys Thr Leu Val Thr Phe Phe Gly Gly Thr
   1               5                  10                   15

GGT GAT TTA GCA AAG CGT AAG CTT TAC CCA TCA GTT TTC AAC CTC TAC         215
Gly Asp Leu Ala Lys Arg Lys Leu Tyr Pro Ser Val Phe Asn Leu Tyr
            20                  25                  30

AAA AAA GGA TAC TTA CAA GAA CAC TTT GCC ATT GTT GGG ACA GCA CGT         263
Lys Lys Gly Tyr Leu Gln Glu His Phe Ala Ile Val Gly Thr Ala Arg
            35                  40                  45

CAA CAA TTA AGT GAT GAC GAG TTT AAG CAA TTG GTT CGT GAT TCA ATT         311
Gln Gln Leu Ser Asp Asp Glu Phe Lys Gln Leu Val Arg Asp Ser Ile
        50                  55                  60

AAA GAC TTT ACT GAA GAT CAA GCA CAA GCC GAA GCG TTT ATT GCG CAT         359
Lys Asp Phe Thr Glu Asp Gln Ala Gln Ala Glu Ala Phe Ile Ala His
    65                  70                  75

TTT TCT TAC CGT GCG CAC GAT GTC ACA GAT GCC GCT TCT TAT GGT ATC         407
Phe Ser Tyr Arg Ala His Asp Val Thr Asp Ala Ala Ser Tyr Gly Ile
80                  85                  90                  95

TTG AAG TCA GCG ATC GAA GAA GCA GCA ACC AAA TTT GAC ATT GAT GGC         455
Leu Lys Ser Ala Ile Glu Glu Ala Ala Thr Lys Phe Asp Ile Asp Gly
                100                 105                 110

AAT CGT ATT TTC TAT ATG TCA GTT GCC CCT CGT TTC TTC GGT ACA ATC         503
Asn Arg Ile Phe Tyr Met Ser Val Ala Pro Arg Phe Phe Gly Thr Ile
            115                 120                 125

GCT AAA TAT TTG AAA TCA GAA GGT TTG CTA GCT GAG ACT GGC TAC AAT         551
Ala Lys Tyr Leu Lys Ser Glu Gly Leu Leu Ala Glu Thr Gly Tyr Asn
        130                 135                 140

CGT TTG ATG ATT GAA AAG CCT TTT GGT ACA TCA TAC GCC ACC GCA GAA         599
Arg Leu Met Ile Glu Lys Pro Phe Gly Thr Ser Tyr Ala Thr Ala Glu
    145                 150                 155

GAA TTG CAA AGT GAT TTG GAA AAT GCA TTT GAT GAT GAC CAA CTG TTC         647
Glu Leu Gln Ser Asp Leu Glu Asn Ala Phe Asp Asp Asp Gln Leu Phe
160                 165                 170                 175

CGT ATT GAC CAC TAT CTT GGA AAA GAA ATG GTA CAA AAT ATT GCA GCA         695
Arg Ile Asp His Tyr Leu Gly Lys Glu Met Val Gln Asn Ile Ala Ala
                180                 185                 190

TTA CGT TTT GGT AAC CCA ATC TTT GAT GCC GCT TGG AAT AAG GAC TAT         743
Leu Arg Phe Gly Asn Pro Ile Phe Asp Ala Ala Trp Asn Lys Asp Tyr
            195                 200                 205

ATC AAA AAC GTA CAA GTA ACT TTG GCT GAA GTT CTA GGT GTT GAA GAG         791
```

| | | | | | | | | | | | | | | | | |
|---|---|---|---|---|---|---|---|---|---|---|---|---|---|---|---|---|
| Ile | Lys | Asn | Val | Gln | Val | Thr | Leu | Ala | Glu | Val | Leu | Gly | Val | Glu | Glu | |
| | | 210 | | | | | 215 | | | | 220 | | | | | |
| CGT | GCT | GGT | TAC | TAC | GAT | ACC | ACT | GGC | GCC | CTT | TTG | GAT | ATG | ATT | CAA | 839 |
| Arg | Ala | Gly | Tyr | Tyr | Asp | Thr | Thr | Gly | Ala | Leu | Leu | Asp | Met | Ile | Gln | |
| | 225 | | | | | 230 | | | | | 235 | | | | | |
| AAC | CAC | ACA | ATG | CAA | ATT | GTT | GGT | TGG | TTA | GCA | ATG | GAA | AAA | CCT | GAA | 887 |
| Asn | His | Thr | Met | Gln | Ile | Val | Gly | Trp | Leu | Ala | Met | Glu | Lys | Pro | Glu | |
| 240 | | | | | 245 | | | | | 250 | | | | | 255 | |
| TCA | TTC | AAT | GAT | AAG | GAT | ATC | CGT | GCA | GCT | AAA | AAC | GCC | GCC | TTC | AAT | 935 |
| Ser | Phe | Asn | Asp | Lys | Asp | Ile | Arg | Ala | Ala | Lys | Asn | Ala | Ala | Phe | Asn | |
| | | | | 260 | | | | | 265 | | | | | 270 | | |
| GCA | TTA | AAG | ATT | TAT | AAC | GAA | GAA | GAA | GTG | AAT | AAG | TAC | TTC | GTT | CGT | 983 |
| Ala | Leu | Lys | Ile | Tyr | Asn | Glu | Glu | Glu | Val | Asn | Lys | Tyr | Phe | Val | Arg | |
| | | | 275 | | | | | 280 | | | | | 285 | | | |
| GCA | CAA | TAT | GGT | GCT | GGT | GAT | ACA | GCT | GAT | TAC | AAG | CCA | TAT | TTG | GAA | 1031 |
| Ala | Gln | Tyr | Gly | Ala | Gly | Asp | Thr | Ala | Asp | Tyr | Lys | Pro | Tyr | Leu | Glu | |
| | | 290 | | | | | 295 | | | | | 300 | | | | |
| GAA | GCA | GAT | GTC | CCT | GCT | GAC | TCA | AAG | AAC | AAC | ACA | TTC | ATT | GCT | GGT | 1079 |
| Glu | Ala | Asp | Val | Pro | Ala | Asp | Ser | Lys | Asn | Asn | Thr | Phe | Ile | Ala | Gly | |
| | 305 | | | | | 310 | | | | | 315 | | | | | |
| GAA | TTG | CAG | TTC | GAT | TTG | CCA | CGT | TGG | GAA | GGT | GTT | CCT | TTC | TAT | GTT | 1127 |
| Glu | Leu | Gln | Phe | Asp | Leu | Pro | Arg | Trp | Glu | Gly | Val | Pro | Phe | Tyr | Val | |
| 320 | | | | | 325 | | | | | 330 | | | | | 335 | |
| CGT | TCA | GGT | AAG | CGT | TTG | GCT | GCC | AAG | CAA | ACA | CGT | GTT | GAT | ATT | GTA | 1175 |
| Arg | Ser | Gly | Lys | Arg | Leu | Ala | Ala | Lys | Gln | Thr | Arg | Val | Asp | Ile | Val | |
| | | | 340 | | | | | 345 | | | | | 350 | | | |
| TTT | AAG | GCT | GGC | ACA | TTC | AAC | TTT | GGT | TCA | GAA | CAA | GAA | GCA | CAA | GAA | 1223 |
| Phe | Lys | Ala | Gly | Thr | Phe | Asn | Phe | Gly | Ser | Glu | Gln | Glu | Ala | Gln | Glu | |
| | | | 355 | | | | | 360 | | | | | 365 | | | |
| TCA | GTA | CTC | TCA | ATC | ATC | ATT | GAT | CCA | AAG | GGT | GCT | ATT | GAA | TTG | AAG | 1271 |
| Ser | Val | Leu | Ser | Ile | Ile | Ile | Asp | Pro | Lys | Gly | Ala | Ile | Glu | Leu | Lys | |
| | | 370 | | | | | 375 | | | | | 380 | | | | |
| CTT | AAC | GCT | AAG | TCA | GTT | GAA | GAT | GCC | TTC | AAC | ACC | CGC | ACA | ATC | AAC | 1319 |
| Leu | Asn | Ala | Lys | Ser | Val | Glu | Asp | Ala | Phe | Asn | Thr | Arg | Thr | Ile | Asn | |
| | 385 | | | | | 390 | | | | | 395 | | | | | |
| TTG | GAT | TGG | GCA | GTA | TCT | GAT | GAA | GAC | AAG | AAG | AAC | ACA | CCA | GAA | CCA | 1367 |
| Leu | Asp | Trp | Ala | Val | Ser | Asp | Glu | Asp | Lys | Lys | Asn | Thr | Pro | Glu | Pro | |
| 400 | | | | | 405 | | | | | 410 | | | | | 415 | |
| TAC | GAA | CGT | ATG | ATT | CAC | GAT | ACA | ATG | AAT | GGT | GAC | GGA | TCA | AAC | TTT | 1415 |
| Tyr | Glu | Arg | Met | Ile | His | Asp | Thr | Met | Asn | Gly | Asp | Gly | Ser | Asn | Phe | |
| | | | | 420 | | | | | 425 | | | | | 430 | | |
| GCT | GAT | TGG | AAC | GGT | GTA | TCA | ATT | GCT | TGG | AAG | TTT | GTT | GAC | GCA | ATT | 1463 |
| Ala | Asp | Trp | Asn | Gly | Val | Ser | Ile | Ala | Trp | Lys | Phe | Val | Asp | Ala | Ile | |
| | | | 435 | | | | | 440 | | | | | 445 | | | |
| ACT | GCC | GTT | TAC | GAT | GCA | GAT | AAA | GCA | CCA | TTG | GAG | ACA | TAT | AAG | TCA | 1511 |
| Thr | Ala | Val | Tyr | Asp | Ala | Asp | Lys | Ala | Pro | Leu | Glu | Thr | Tyr | Lys | Ser | |
| | | 450 | | | | | 455 | | | | | 460 | | | | |
| GGT | TCA | ATG | GGT | CCT | GAA | GCA | TCA | GAC | AAG | CTA | TTA | GCT | GAA | AAT | GGC | 1559 |
| Gly | Ser | Met | Gly | Pro | Glu | Ala | Ser | Asp | Lys | Leu | Leu | Ala | Glu | Asn | Gly | |
| | 465 | | | | | 470 | | | | | 475 | | | | | |
| GAT | GCT | TGG | GTA | TTT | AAA | GGA | TAAGCACATT | | TAAAAGACC | | ATCAAACAAA | | | | | 1610 |
| Asp | Ala | Trp | Val | Phe | Lys | Gly | | | | | | | | | | |
| 480 | | | | 485 | | | | | | | | | | | | |

TCTTTGTTTG ACGGTCTTTT TATATTGTCT GATTTAAGAT GCGTTTGGTT TCACGGAAAA　　1670

CGGCTGACAA ATTGGTGTAT TGATCC　　1696

( 2 ) INFORMATION FOR SEQ ID NO:2:

( i ) SEQUENCE CHARACTERISTICS:
        ( A ) LENGTH: 486 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Val | Ser | Glu | Ile | Lys | Thr | Leu | Val | Thr | Phe | Phe | Gly | Gly | Thr | Gly |
|---|---|---|---|---|---|---|---|---|---|---|---|---|---|---|---|
| 1 | | | | 5 | | | | | 10 | | | | | 15 | |
| Asp | Leu | Ala | Lys | Arg | Lys | Leu | Tyr | Pro | Ser | Val | Phe | Asn | Leu | Tyr | Lys |
| | | | 20 | | | | | 25 | | | | | 30 | | |
| Lys | Gly | Tyr | Leu | Gln | Glu | His | Phe | Ala | Ile | Val | Gly | Thr | Ala | Arg | Gln |
| | | 35 | | | | | 40 | | | | | 45 | | | |
| Gln | Leu | Ser | Asp | Asp | Glu | Phe | Lys | Gln | Leu | Val | Arg | Asp | Ser | Ile | Lys |
| | 50 | | | | | 55 | | | | | 60 | | | | |
| Asp | Phe | Thr | Glu | Asp | Gln | Ala | Gln | Ala | Glu | Ala | Phe | Ile | Ala | His | Phe |
| 65 | | | | | 70 | | | | 75 | | | | | | 80 |
| Ser | Tyr | Arg | Ala | His | Asp | Val | Thr | Asp | Ala | Ala | Ser | Tyr | Gly | Ile | Leu |
| | | | | 85 | | | | | 90 | | | | | 95 | |
| Lys | Ser | Ala | Ile | Glu | Glu | Ala | Ala | Thr | Lys | Phe | Asp | Ile | Asp | Gly | Asn |
| | | | 100 | | | | | 105 | | | | | 110 | | |
| Arg | Ile | Phe | Tyr | Met | Ser | Val | Ala | Pro | Arg | Phe | Phe | Gly | Thr | Ile | Ala |
| | | 115 | | | | | 120 | | | | | 125 | | | |
| Lys | Tyr | Leu | Lys | Ser | Glu | Gly | Leu | Leu | Ala | Glu | Thr | Gly | Tyr | Asn | Arg |
| | 130 | | | | | 135 | | | | | 140 | | | | |
| Leu | Met | Ile | Glu | Lys | Pro | Phe | Gly | Thr | Ser | Tyr | Ala | Thr | Ala | Glu | Glu |
| 145 | | | | | 150 | | | | 155 | | | | | | 160 |
| Leu | Gln | Ser | Asp | Leu | Glu | Asn | Ala | Phe | Asp | Asp | Gln | Leu | Phe | Arg | |
| | | | | 165 | | | | | 170 | | | | | 175 | |
| Ile | Asp | His | Tyr | Leu | Gly | Lys | Glu | Met | Val | Gln | Asn | Ile | Ala | Ala | Leu |
| | | | 180 | | | | | 185 | | | | | 190 | | |
| Arg | Phe | Gly | Asn | Pro | Ile | Phe | Asp | Ala | Ala | Trp | Asn | Lys | Asp | Tyr | Ile |
| | | 195 | | | | | 200 | | | | | 205 | | | |
| Lys | Asn | Val | Gln | Val | Thr | Leu | Ala | Glu | Val | Leu | Gly | Val | Glu | Glu | Arg |
| | 210 | | | | | 215 | | | | | 220 | | | | |
| Ala | Gly | Tyr | Tyr | Asp | Thr | Thr | Gly | Ala | Leu | Leu | Asp | Met | Ile | Gln | Asn |
| 225 | | | | | 230 | | | | 235 | | | | | | 240 |
| His | Thr | Met | Gln | Ile | Val | Gly | Trp | Leu | Ala | Met | Glu | Lys | Pro | Glu | Ser |
| | | | | 245 | | | | | 250 | | | | | 255 | |
| Phe | Asn | Asp | Lys | Asp | Ile | Arg | Ala | Ala | Lys | Asn | Ala | Ala | Phe | Asn | Ala |
| | | | 260 | | | | | 265 | | | | | 270 | | |
| Leu | Lys | Ile | Tyr | Asn | Glu | Glu | Glu | Val | Asn | Lys | Tyr | Phe | Val | Arg | Ala |
| | | 275 | | | | | 280 | | | | | 285 | | | |
| Gln | Tyr | Gly | Ala | Gly | Asp | Thr | Ala | Asp | Tyr | Lys | Pro | Tyr | Leu | Glu | Glu |
| | 290 | | | | | 295 | | | | | 300 | | | | |
| Ala | Asp | Val | Pro | Ala | Asp | Ser | Lys | Asn | Asn | Thr | Phe | Ile | Ala | Gly | Glu |
| 305 | | | | | 310 | | | | 315 | | | | | | 320 |
| Leu | Gln | Phe | Asp | Leu | Pro | Arg | Trp | Glu | Gly | Val | Pro | Phe | Tyr | Val | Arg |
| | | | | 325 | | | | | 330 | | | | | 335 | |
| Ser | Gly | Lys | Arg | Leu | Ala | Ala | Lys | Gln | Thr | Arg | Val | Asp | Ile | Val | Phe |
| | | | 340 | | | | | 345 | | | | | 350 | | |
| Lys | Ala | Gly | Thr | Phe | Asn | Phe | Gly | Ser | Glu | Gln | Glu | Ala | Gln | Glu | Ser |
| | | 355 | | | | | 360 | | | | | 365 | | | |
| Val | Leu | Ser | Ile | Ile | Ile | Asp | Pro | Lys | Gly | Ala | Ile | Glu | Leu | Lys | Leu |
| | 370 | | | | | 375 | | | | | 380 | | | | |
| Asn | Ala | Lys | Ser | Val | Glu | Asp | Ala | Phe | Asn | Thr | Arg | Thr | Ile | Asn | Leu |
| 385 | | | | | 390 | | | | 395 | | | | | | 400 |
| Asp | Trp | Ala | Val | Ser | Asp | Glu | Asp | Lys | Lys | Asn | Thr | Pro | Glu | Pro | Tyr |
| | | | | 405 | | | | | 410 | | | | | 415 | |

```
Glu Arg Met Ile His Asp Thr Met Asn Gly Asp Gly Ser Asn Phe Ala
            420             425             430

Asp Trp Asn Gly Val Ser Ile Ala Trp Lys Phe Val Asp Ala Ile Thr
        435             440             445

Ala Val Tyr Asp Ala Asp Lys Ala Pro Leu Glu Thr Tyr Lys Ser Gly
    450             455             460

Ser Met Gly Pro Glu Ala Ser Asp Lys Leu Leu Ala Glu Asn Gly Asp
465             470             475             480

Ala Trp Val Phe Lys Gly
                485
```

( 2 ) INFORMATION FOR SEQ ID NO:3:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
RTTTGAACC ATTTCTTTWC CTAAATAATG ATCAATWCKA AATAATTGRT TATCATCAAA        60

AGCGTTTTCA AA        72
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Phe Leu Leu Lys Ser Pro Ser Tyr Asp Lys
1               5                   10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Phe Leu Leu Lys Ser Pro Ser Tyr Val Lys
1               5                   10
```